(12) United States Patent
Chang et al.

(10) Patent No.: US 7,312,076 B2
(45) Date of Patent: Dec. 25, 2007

(54) LACTOBACILLI EXPRESSING BIOLOGICALLY ACTIVE POLYPEPTIDES AND USES THEREOF

(75) Inventors: Chia-Hwa Chang, Mountain View, CA (US); David A. Simpson, Redwood City, CA (US); Theresa Li-Yun Chang, Los Gatos, CA (US); Qiang Xu, Cupertino, CA (US); John A. Lewicki, Los Gatos, CA (US)

(73) Assignee: Osel, Inc., Santa Clara, CA (US)

( * ) Notice: Subject to any disclaimer, the term of this patent is extended or adjusted under 35 U.S.C. 154(b) by 0 days.

(21) Appl. No.: 11/620,588

(22) Filed: Jan. 5, 2007

(65) Prior Publication Data

US 2007/0117197 A1    May 24, 2007

Related U.S. Application Data

(62) Division of application No. 10/383,834, filed on Mar. 6, 2003, now Pat. No. 7,179,458.

(60) Provisional application No. 60/362,945, filed on Mar. 8, 2002.

(51) Int. Cl.
    *C12N 15/00* (2006.01)
(52) U.S. Cl. .................................. 435/320.1
(58) Field of Classification Search ............... 435/320.1
    See application file for complete search history.

(56) References Cited

U.S. PATENT DOCUMENTS

| | | | |
|---|---|---|---|
| 5,705,160 A | 1/1998 | Bruce et al. | |
| 5,733,540 A | 3/1998 | Lee | |
| 5,804,179 A | 9/1998 | Bruce et al. | |
| 5,821,081 A | 10/1998 | Boyd et al. | |
| 6,180,100 B1 | 1/2001 | Bruce et al. | |
| 6,193,982 B1 | 2/2001 | Boyd | |
| 6,277,370 B1 | 8/2001 | Cavaliere Ved. Vesely et al. | |
| 6,641,818 B1 * | 11/2003 | Spear et al. ............. | 424/204.1 |

FOREIGN PATENT DOCUMENTS

WO    WO 96/11277 A1    4/1996

OTHER PUBLICATIONS

Beninati, Concetta et al.; "Therapy of mucosal candidiasis by expression of an anti-idiotype in human commensal bacteria"; *Nature Biotechnology* 18:1060-1064 (Oct. 2000).

Giomarelli, Barbara et al.; "The microbicide cyanovirin-N expressed on the surface of commensal bacterium *Streptococcus goronii* captures HIV-1"; *AIDS* 16:1351-1356 (Jul. 2002).

Kruger, Carina et al.; "In situ delivery of passive immunity by lactobacilli producting single-chain antibodies"; *Nature Biotechnology* 20:702-706 (Jul. 2002).

Steidler, Lothar et al.; "Treatment of *Murine colitis* by *Lactococcus lactis* secreting interleukin-10"; *Science* 289:1352-1355 (Aug. 25, 2000).

Vallor, Ana C. et al.; "Factors associated with acquisition of, or persistent colonization by, vaginal lactobacilli: role of hydrogen peroxide production"; *The Journal of Infectious Diseases* 184:1431-1436 (2001).

\* cited by examiner

*Primary Examiner*—Brian Whiteman
(74) *Attorney, Agent, or Firm*—Townsend and Townsend and Crew LLP

(57) ABSTRACT

The present invention relates to *Lactobacillus* species recombinantly altered to express a biologically active protein. The invention also related to methods of providing the bacteria to the vagina.

12 Claims, 6 Drawing Sheets

A. Shuttle vector

B. Expression cassette for protein secretion

C. Expression cassette for protein anchoring

LACTOBACILLI EXPRESSING BIOLOGICALLY ACTIVE POLYPEPTIDES AND USES THEREOF

CROSS-REFERENCES TO RELATED APPLICATIONS

This application is a division of U.S. patent application Ser. No. 10/383,834, now U.S. Pat. No. 7,179,458, filed Mar. 6, 2003, which claims the benefit of U.S. Provisional Application No. 60/362,945, filed Mar. 8, 2002. All of the aforementioned applications are hereby incorporated by reference in their entireties and for all purposes.

STATEMENT AS TO RIGHTS TO INVENTIONS MADE UNDER FEDERALLY SPONSORED RESEARCH OR DEVELOPMENT

This invention was made with Government support under SBIR phase I Grant No. 1 R43 AI46403-01. The government has certain rights in this invention.

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The mucosal membranes of all humans are naturally colonized by bacteria. Recent scientific evidence has documented the fact that these bacteria interact closely with cells and tissues of the body to regulate natural biological processes. It has become increasingly evident that this mucosal microflora also contributes substantially to numerous diseases affecting cells and tissues of humans.

Generally, domination of the microflora within the vagina and gastrointestinal tract, by lactobacilli and related bacteria, is associated with good health. Natural strains of lactobacilli have been administered for many years as "probiotics" for the purpose of maintaining a healthy microflora within these locations and preventing infection. It is well established that these "healthy bacteria" compete with pathogenic organisms, such as bacteria, viruses and fungi to limit the development and progression of pathogen associated diseases. Nevertheless, this microflora is a fragile and dynamic environment with the natural turnover and disruption of the healthy microflora being associated with the establishment of opportunistic infections. Consequently, approaches to maintain, or even enhance, the integrity and natural properties of the microflora, as a means of preventing or treating disease, would be coveted by the biomedical community.

Currently, the predominant mode of transmission of viruses, like human immunodeficiency virus (HIV) and herpes simplex virus type 2 (HSV-2), is via heterosexual contact. Women are particularly at risk for infection by sexually transmitted viruses, as the efficiency of HIV and HSV-2 transmission from male to female is greater than for the reverse (al-Nozha et al., *J. Acquir. Immune. Defic. Syndr.* 3:193-194 (1990); Wald et al., *JAMA* 285:3100-3106 (2001)). The first natural line of defense against disease transmission for women during heterosexual contact is the mucosal barrier in the vagina. In healthy American and European women of childbearing age, either *Lactobacillus crispatus* or *L. jensenii* are most commonly the predominant bacteria colonizing the vaginal mucosa (Antonio et al., *J. Infect. Dis.* 180:1950-1956 (1999); Vasquez et al., *J. Clin. Microbiol.* 40:2746-2749 (2002)). These lactobacilli secrete lactic acid as a byproduct of metabolism, serving to acidify the vaginal mucosa and to keep the numbers of competing pathogenic microorganisms relatively low. Additionally, the predominance of lactobacilli in the vaginal microflora of healthy women has been associated with a lowered incidence of HIV acquisition, perhaps correlating with the observed antagonistic effects of metabolic byproducts of lactobacilli (lactic acid and peroxide), on the infectivity of the HIV virus in vitro. Therefore, the association of beneficial lactobacilli with the vaginal mucosa can be considered together as a protective "biofilm". Sexually transmitted viruses like HIV and HSV-2 must first successfully traverse this protective matrix before infecting a host and causing disease.

The mucosal microflora contributes to many other local diseases affecting mucosal surfaces. For instance, the etiology of inflammatory bowel diseases, including ulcerative colitis and Crohn's disease may arise from inappropriate interactions between a disrupted mucosal microflora and cells and tissues of the host. A means of modulating the properties of bacteria within the mucosal flora could aid in the prevention and or treatment of these diseases, as well as related conditions affecting mucosal surfaces.

The present invention addresses these and other problems.

BRIEF SUMMARY OF THE INVENTION

The present invention provides mucosal surface-colonizing *Lactobacillus jensenii* bacteria recombinantly altered to express a biologically active protein. In some embodiments, the mucosal surface resides within the vagina. In some embodiments, the mucosal surface resides within the gastrointestinal tract. In some embodiments, the mucosal surface is a human mucosal surface.

In some embodiments, the protein requires a disulfide bond to be biologically active. In some embodiments, the biologically active protein is secreted.

In some embodiments, the biologically active protein is on the bacterial surface. In some embodiments, the protein comprises a signal sequence selected from the group consisting of SEQ ID NO:1, SEQ ID NO:2 and SEQ ID NO:3. In some embodiments, the biologically active protein comprises a cell wall anchoring signal sequence. In some embodiments, the cell wall anchoring signal sequence comprises SEQ ID NO:4 or SEQ ID NO:5.

In some embodiments, the biologically active protein binds to a pathogen when the biologically active protein is contacted with a pathogen. In some embodiments, the pathogen is a bacterial pathogen. In some embodiments, the pathogen is a fungal pathogen. In some embodiments, the pathogen is a viral pathogen.

In some embodiments, the viral pathogen is HIV. In some embodiments, the biologically active protein is CD4 or an HIV-binding fragment of CD4. In some embodiments, the biologically active protein is two-domain CD4 (2D-CD4). In some embodiments, the biologically active protein is cyanovirin-N or a virus-binding fragment of cyanovirin-N. In some embodiments, the viral pathogen is HSV. In some embodiments, the biologically active protein binds to HSV. In some embodiments, the protein is herpes virus entry mediator C (HveC) or a virus-binding fragment of HveC.

In some embodiments, the biologically active protein is a therapeutic polypeptide. In some embodiments, the biologically active protein is a polypeptide vaccine.

In some embodiments, the biologically active protein has a molecular weight of between 500 and 40,000 daltons.

The invention also provides methods of providing a biologically active protein to a mammalian mucosal surface. In some embodiments, the methods comprise, contacting the mucosal surface with *Lactobacillus jensenii* bacteria recombinantly altered to express a biologically active protein in an amount able to be detected in a sample collected from the mucosal surface. In some embodiments, the mucosal surface resides within the vagina. In some embodiments, the mucosal surface resides within the gastrointestinal tract.

In some embodiments, the contacting step comprises orally administering the *Lactobacillus jensenii* bacteria. In some embodiments, the contacting step comprises rectally administering the *Lactobacillus jensenii* bacteria. In some embodiments, the contacting step comprises vaginally administering the *Lactobacillus jensenii* bacteria.

The present invention also provides expression cassettes comprising a polynucleotide encoding a heterologous bacterial signal sequence substantially identical to SEQ ID NO:2. In some embodiments, the expression cassette comprises a polynucleotide encoding a polypeptide, wherein the amino-terminus of the polypeptide comprises a heterologous bacterial signal sequence at least 95% identical to SEQ ID NO:2. In some embodiments, the bacterial signal sequence comprises SEQ ID NO:2.

The present invention also provides vectors comprising the expression cassette and host cells comprising such vectors. In some embodiments, the cell is a gram-positive bacterium.

DEFINITIONS

A "vaginal colonizing bacteria" refers to bacteria that naturally colonize the vagina or recombinantly altered strains of such bacteria. Examples of vaginal colonizing bacteria include, e.g., *L. jensenii* and *L. crispatus*.

A "biologically active protein" refers to an amino acid sequence that has the biological activity (i.e., can participate in the molecular mechanisms) of the amino acid sequence within, or outside of, a native cell. Activity of a protein includes, e.g., its immunogenicity. Therefore, polypeptide vaccines are biologically active proteins. Typically, the amino acid sequence forms the three-dimensional structure formed by the amino acid sequence within or outside of the native cell.

A polypeptide "associated with a bacterial surface" refers to a polypeptide attached or imbedded in a bacterial membrane or cell wall matrix or biofilm.

A "pathogen" refers to a virus, bacteria, fungus, protozoa or other microscopic organism that causes disease of harm to a host.

"2D-CD4" refers to the first approximately 183 amino acids of 2-domain CD4. CD4 is a cell-surface glycoprotein found on the mature helper T cells and immature thymocytes, as well as monocytes and macrophages. 2D-CD4 binds to HIV-1 gp120 with the same affinity as the intact protein (Salzwedel et al., *J. Virol.* 74:326-333 (2000)), and contains the binding site for gp120. CD4 contains an amino-terminal extracellular domain (amino acid residues 1 to 371), a transmembrane region (372 to 395) and a cytoplasmic tail (396 to 433).

A bacterial "biofilm" refers to a complex network of different bacteria and extracellular matrix materials secreted by the bacteria.

The term "gene" means the segment of DNA involved in producing a polypeptide chain; it includes regions preceding and following the coding region (leader and trailer).

A "therapeutic protein" or "therapeutic polypeptide" refers to a polypeptide possessing biological activity that can be used for the prevention and/or treatment of disease. Examples of therapeutic polypeptides include those capable of preventing, inhibiting, stabilizing or reversing an inherited or noninherited genetic defect in metabolism, immune regulation, hormonal regulation, enzymatic or membrane associated structural function. For example, therapeutic protein can replace an absent or defective cellular protein or enzyme, or supplement production of a defective or low expressed cellular protein or enzyme.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab')$_2$, a dimer of Fab which itself is a light chain joined to $V_H$-$C_H$1 by a disulfide bond. The F(ab')$_2$ may be reduced under mild conditions to break the disulfide linkage in the hinge region, thereby converting the F(ab')$_2$ dimer into an Fab' monomer. The Fab' monomer is essentially an Fab with part of the hinge region (see, Paul (Ed.) *Fundamental Immunology*, Third Edition, Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 70% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 91%, 92%, 93%, 94%, 95%, 96%, 97%, 98 or 99% compared to a reference sequence (e.g., SEQ ID NO:2) using the programs described herein, such as BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity bacterium of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Accelrys, 9685 Scranton Road, San Diego, Calif.), or by manual alignment and visual inspection.

An example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Conservatively modified variants of the polypeptides described herein are encompassed by the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform to codon preference in a specific host cell.

The term "recombinant" or "recombinantly altered" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" is a nucleic acid, generated recombinantly or synthetically, with a series of specified nucleic acid elements that permit transcription of a particular nucleic acid in a host cell. The expression cassette can be part of a plasmid, virus, or nucleic acid fragment. Typically, the expression vector includes a nucleic acid to be transcribed operably linked to a promoter.

DETAILED DESCRIPTION OF THE INVENTION

I. Introduction

Figure 1:
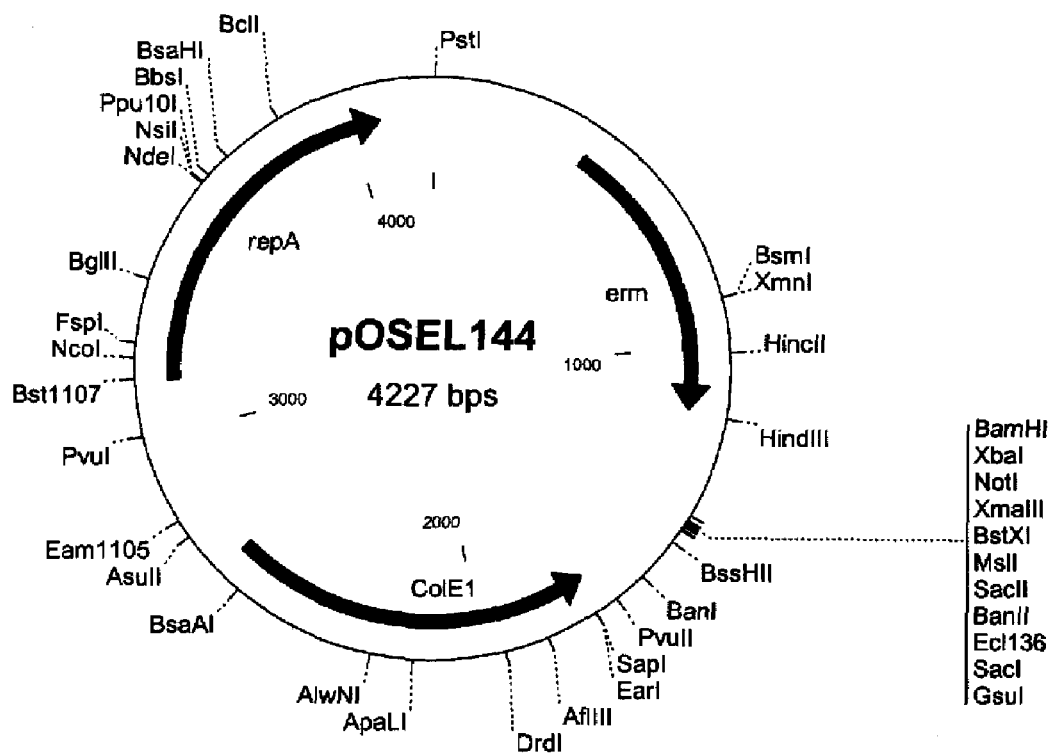
FIG. 1 illustrates the diagram of pOSEL144 a shuttle vector between *E. coli* and *Lactobacillus* sp (A). The repA and erm genes are derived from *L. reuteri* and the ColE1 replicon is from pBluescript. A multiple cloning site for insertion of target gene is located between erm and ColE 1 ori. The expression cassettes for either protein secretion (B) or anchoring (C) contain unique restriction sites.
Figure 1:
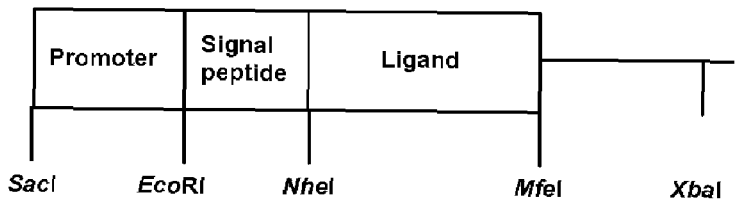
Figure 1:
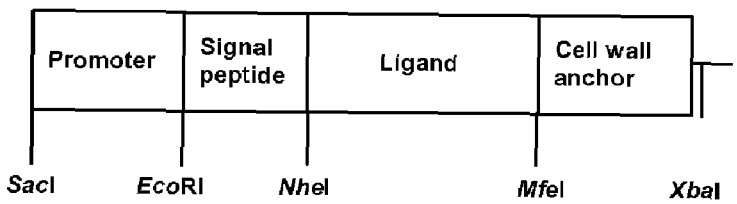

The present invention provides mucosal surface-colonizing species of *Lactobacillus* that are recombinantly altered to express biologically active proteins and uses thereof. The inventors have surprisingly discovered that, in contrast to other mucosal surface-colonizing lactobacilli such as *L. crispatus*, *L. jensenii* can be readily transformed to express biologically active proteins, including proteins of mammalian origin.

Biologically active proteins include, for example, proteins with at least one disulfide bond. Exemplary biologically active proteins include, anti-viral, anti-bacterial or anti-fungal or therapeutic polypeptides, such as anti-inflammatory proteins, growth factors and growth factor antagonists, sugar-binding polypeptides, antibodies and enzymes. The bacteria of the invention are useful, e.g., for expressing biologically active proteins within the vagina or gastrointestinal tract for the purpose of preventing and/or treating diseases.

II. Recombinant Techniques

A. Molecular Biology Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA libraries that are made from cDNA or genomic DNA. The particular sequences can be located by hybridizing with an oligonucleotide probe, the sequence of which can be derived from the sequences disclosed herein or are known in the art, which provide a reference for PCR primers and defines suitable regions for isolating gene-specific probes. Alternatively, where the sequence is cloned into an expression library, the expressed recombinant protein can be detected immunologically with antisera or purified antibodies made against a polypeptide of interest, including those disclosed herein.

Methods for making and screening genomic and cDNA libraries are well known to those of skill in the art (see, e.g., Gubler & Hoffman, *Gene* 25:263-269 (1983); Benton & Davis, *Science*, 196:180-182 (1977); Adams et al. (eds). *Automated DNA Sequencing and Analysis*, Academic Press, London (1994), and Sambrook, supra). Cells expressing a protein of interest are useful sources of RNA for production of a cDNA library.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue or cell and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci.* USA, 72:3961-3965 (1975).

An alternative method combines the use of synthetic oligonucleotide primers with polymerase extension on an mRNA or DNA template. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding a polypeptide of the invention from tissues or cell samples can be derived from the sequences described in the art. For a general overview of PCR, see, Innis et al., *PCR Protocols: A Guide to Methods and Applications*, Academic Press, San Diego (1990).

A polynucleotide encoding a polypeptide of the invention can be cloned using intermediate vectors before transformation into *Lactobacillus*. These intermediate vectors are typically prokaryote vectors or shuttle vectors.

C. Transformation Techniques

Appropriate bacterial host strains are selected for, e.g. their transformation ability, ability for heterologous protein expression, and/or mucosal surface. The bacterial host will be rendered competent for transformation using standard techniques, such as the rubidium chloride method or electroporation (see, e.g., Wei et al., *J. Microbiol. Methods* 21:97-109 (1995).

Transformation of *L. jensenii* by electroporation can be performed by modifying standard methods as described in, e.g., Luchansky et al. (*J. Dairy Sci.* 74: 3293-3302 (1991). Briefly, freshly inoculated *L. jensenii* are cultured in MRS broth (e.g., to 0.6-0.7 at $OD_{600}$ at 37° C. and 5% $CO_2$). The bacterial cells are harvested, washed and re-suspended in a cold (e.g., 4° C.) solution of sucrose and $MgCl_2$. Competent cells are then mixed with DNA and placed in a chilled gap cuvette and electroporated. Afterward, cells are allowed to recover in pre-warmed broth (e.g., for about two hours at 37° C.), prior to being plated on selective agar plate containing an antibiotic other selective agent.

Optionally, antibiotic pretreatment of the user can be used to pre-clear the mucosal surface of resident bacteria prior to introduction of the bacteria of the invention into the vagina or gastrointestinal tract. See, e.g., Freter et al., *Infect. Immun.*, 39:686-703 (1983). Antibiotics can be provided orally or can be applied directly to the vagina.

A first method involves repetitively selecting for rapid colonizing bacteria on animal or human mucosal layers. For example, one applies a wildtype bacterial strain to a mucosal surface and repetitively isolates and in vitro cultures bacteria, returning at each step to the mucosal surface. Ultimately, a bacterium with an enhanced colonizing ability is obtained.

A second method involves expression of fusion proteins on the surface of recombinant bacteria. The fusion protein consists of a host-binding domain linked to a polypeptide of interest. The host-binding domain will allow the bacteria to bind to certain determinants (protein or carbohydrate) on a selected host mucosal surface with high affinity, thus conferring the bacteria a survival advantage over the resident microflora.

The third method involves induction of resident microflora to express a heterologous protein by introducing the gene via bacteriophage. A number of bacteriophage vectors have been developed for use in different bacteria. For example, a bacteriophage vector based on the temperate bacteriophage (φadh can be used (see, e.g., Raya et al., *J. Bacteriol.* 174:5584-5592 (1992) and Fremaux et al., *Gene* 125:61-66 (1993)). This vector undergoes site-specific integration into the host chromosome at defined phage (attP) and bacterial (attB) attachment sites. Similarly, *Lactobacillus*-specific bacteriophage can be used to transduce vectors or other polynucleotides into the *Lactobacillus* chromosome. *Lactobacillus*-specific phage include mv4 (Auvray et al, *J. Bacteriol.*, 179:1837-1845 (1997)), (φadh (Fremaux et al., *Gene* 126:61-66 (1993)), (φgle (Kakikawa et al, *Gene* 175: 157-165 (1996), and those belonged to *Bradley's groups A or B in vaginal Lactobacillus isolates* (Kilic et al., Clin. Diagn. Lab. Immunol. 8:31-39 (2001)).

Certain agents that do not irritate mucosal epithelial cells may also be added to a unit dose of the bacteria in capsules or tablets to aid in colonization. Many bacteria on mucosal surfaces secrete capsular materials that coalesce to form a biofilm that covers the entire mucosal surface. It may be beneficial to add an enzyme that digests this biofilm material to promote penetration of the engineered bacteria into the biofilm for more successful colonization. The enzymes include DNAses, peptidases, collagenases, hyaluronidases, and other carbohydrate degrading enzymes. Antibiotics to which the engineered bacteria itself is not susceptible may also be added to decrease the number of resident bacteria on the mucosal surface in order to make room for the engineered bacteria.

D. Expression

Expression cassettes of the invention can include a variety of components to regulate expression and localization of the polypeptides of the invention. For example, expression cassettes can include promoter elements, sequences encoding signal sequences, a coding sequence for the polypeptide of interest and anchor sequences.

Expression of the heterologous polynucleotides or polypeptides can be constitutive (e.g., using $P_{59}$ (van der Vossen et al., *Appl. Environ. Microbiol.* 58:3142-3149 (1992)) or $P_{23}$ (Elliot et al., *Cell* 36:211-219 (1984)) promoters). Alternatively, expression can be under the control of an inducible promoter. For example, the *Bacillus* amylase (Weickert et al., *J. Bacteriol.* 171:3656-66 (1989)) or xylose (Kim et al. *Gene* 181:71-76 (1996)) promoters as well as the *Lactococcus* nisin promoter (Eichenbaum et al., *Appl. Environ. Microbiol.* 64:2763-2769 (1998)) can be used to drive inducible expression. In addition, acid or alkaline-induced promoters can be used. For example, promoters that are active under the relatively acidic conditions of the vagina (e.g., those described in U.S. Pat. No. 6,242,194) can be used. Alternatively, promoters can be used that are induced upon changes in the vagina in response to semen. For example, alkaline-induced promoters are used to induce expression in response to the increased alkaline conditions of the vagina resulting from the introduction of semen.

A variety of signal and anchor sequences are known to direct expression of polypeptides to the membrane, extracellular space or the cell wall (e.g., by covalent attachment to peptidoglycan). Exemplary signal sequences include the signal sequence from α-Amylase of L. amylovorus (Giraud & Cuny, Gene 198:149-157 (1997)) or the signal sequence from the S-layer gene (cbsA) of L. crispatus (e.g., MKKN-LRIVSAAAAALLAVAPVAA (SEQ ID NO:1) or MKKN-LRIVSAAAAALLAVATVSA (SEQ ID NO:2)). Signal sequences are typically located at the amino-terminus of a polypeptide.

Anchor sequences are typically located at the carboxyl terminus of an encoded protein sequence. Anchor sequences include, e.g., a cell wall associated sequence; the sequence LPQ(S/A/T)(G/A), where residues in parentheses indicate different options at that position; and a hydrophobic sequence, and, optionally, a charged sequence. In some embodiments, the anchoring sequence comprises binding assays. For anti-inflammatory molecules, the expressed polypeptide can be assayed for its ability to antagonize substances that promote inflammation.

When synthesizing a gene for improved expression in a host cell, it is desirable to design the gene such that its frequency of codon usage approaches the frequency of preferred codon usage of the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons.

The polynucleotide sequence encoding a particular polypeptide can be altered to coincide with the codon usage of a particular host. For example, the codon usage of Lactobacillus can be used to derive a polynucleotide that encodes a polypeptide of the invention and comprises preferred Lactobacillus codons. The frequency of preferred codon usage exhibited by a host cell can be calculated by averaging the frequency of preferred codon usage in a large number of genes expressed by the host cell. This analysis is preferably limited to genes that are highly expressed by the host cell. Pouwels & Leunissen (Nucleic Acids Res. 22:929-

(SEQ ID NO:4)
VTRTINVVDPITGKISTSVQTAKFTREDKNSNAGYTDPVTGKTTMNPWTPAKQGLRA

VNVEQIKGYVAKVDGNVDAVVVTPDSANMVVTITYQANKPEGQNITVKKDTVPDP

ADGIKNKDDLPDGTKYTWKEVPDVNSVGEKTGIVTVTFPDGTSVDVKVTVYVDPVV

ESNRDTLSKEANTGNTNVAKAATVTSSKVESKKTLPQTGSKTEQVGILGLAIATVGS

LLGLGVNRKKRQK, (SEQ ID NO:5)
KKAEEVKNNSNATQKEVDDATNNLKQAQNDLDGQTTDKSKLDEAIKSADDTKSTD

KYNNASDDTKSKFDEALKKAEEVKNNSNATQKEVDDATKNLKQAQNDLDGQTTN

KDAINDAIKDANNAKGTDKYNNASDDTKSKFDDALKKAEDVKNDSNANQKEVDD

ATKNLKNTLNNLKGQPAKKANLIASKDNAKIHKQTLLPQTGTETNPLTAIGIGLMAL

GAGIFAKKKRKDDEA.

or sequences substantially identical to SEQ ID NO:4 or SEQ ID NO:5.

Correct localization and folding of a polypeptide can be determined using standard methods. For example, cell wall enriched fractions of Lactobacillus can be obtained by suspending the bacteria in a buffered solution (e.g., 25% sucrose, 1 mM EDTA, 10 mM Tris-HCl, pH 8.0) followed by treatment with cell wall degrading enzymes (e.g., lysozyme and mutanolysin) and then separating out the resulting protoplasts by differential centrifugation (Piard et al., J. Bacteriol. 179:3068-3072 (1997)). Fractions can then be screened by Western blotting to confirm expression within the cell wall.

Folding and biological activity of an expressed polypeptide can also be determined using standard methods. For example, ELISA assays using antibodies specific for the natively folded polypeptide can be used to confirm folding and three-dimensional structure of the polypeptide. Biological activity assays will of course vary depending on the activity of the polypeptide. For example, for polypeptides that bind to viral proteins, the expressed polypeptide can be tested for its ability to bind a viral protein using standard 936 (1994)), for example, provides the frequency of codon usage by highly expressed genes exhibited by various Lactobacillus species. Codon-usage tables are also available via the internet.

III. Proteins of the Invention

The polypeptides of the invention expressed in Lactobacillus sp. can be any polypeptide. Typically, the polypeptides of the invention are expressed under conditions to allow for biological activity of the polypeptides. In some embodiments, a disulfide bond exists in the expressed polypeptide. In some embodiments, the disulfide bond is required for the polypeptide's biological activity.

Polypeptides of the invention can be of any size molecular eight. For example, the polypeptides can be between about 100 and 100,000 daltons, between about 500 and 40,000 daltons, between about 500 and 10,000 daltons, between about 10,000 and 50,000 daltons, or between about 50,000 and 100,000 daltons.

Examples of classes of polypeptides that can be used according to the methods of the invention to prevent or treat pathogen infection include, e.g., anti-viral polypeptides, anti-bacterial polypeptides, anti-fungal polypeptides, and polypeptides that bind to viruses, bacteria or fungi, including antibodies, antibody fragments, or single-chain antibodies.

In some cases, the polypeptides of the invention will be a receptor that viral or bacterial pathogens bind to infect a host. Alternatively, the polypeptides are agents that, e.g., inhibit pathogen replication, viability, entry or otherwise bind to the pathogen. In some embodiments, the polypeptides of the invention bind or inhibit sexually transmitted pathogens and other pathogens transmitted to or from the vagina. For example, since viruses require binding to a receptor on the target cell surface for infection, strategies directed at inhibiting the interaction of a virus with its host receptor are effective at preventing infection.

Exemplary anti-viral polypeptides include, e.g., CD4 or virus-binding fragments thereof (e.g., 2D-CD4) (e.g., Orloff et al., *J. Virol.* 67:1461-1471 (1993)), stable CD4 trimers formed via a trimeric motif (e.g., Yang et al., *J. Virol.* 76:4634-4642 (2002), a dodecameric CD4-Ig fusion protein (Arthos et al., *J. Biol. Chem.* 277:11456-11464 (2002)), α-defensins (e.g. Zhang et al., *Science* 298:995-1000 (2002), CD4 in fusion with a single chain variable region of the 17b monoclonal antibody (mAb) (Dey et al, *J. Virol.* 77:2859-2865 (2003), cyanovirin-N (e.g., Bolmstedt et al., *Mol. Pharmacol.* 59:949-54 (2001)), HveC (e.g., Cocchi et al., *Proc. Natl. Acad. Sci. USA.* 95:15700-15705 (1998)), and intercellular adhesion molecule-1 (ICAM-1). Other embodiments include, e.g., viral receptors or heparin or heparin-like molecules, mannose-binding lectin, including dendritic cell-specific ICAM-3 grabbing nonintegrin (e.g., Geijtenbeek et al., *Cell* 100:587-597 (2000); Feinberg et al., *Science* 294: 2163-2166 (2001)), anti-HSV-1 gp120 single-chain antibody (e.g. Marasco et al., *Proc. Natl. Acad. Sci.* USA. 90:7889-7893 (1993)), human mAb b12, recognizing the CD4-binding site of HIV-1 gp120 (e.g. Saphire et al., *Science* 293:1155-1159 (2001)) or other molecules with similar specificity, including neutralizing antibodies that bind to HSV (e.g., Burioni et al., *Proc. Natl. Acad. Sci. USA.* 91:355-359 (1994)), and HIV-1 entry inhibitory protein (e.g., Root et al., *Science* 291:884-888 (2001); Sia et al., *Proc. Natl. Acad. Sci. USA.* 99:14664-14669 (2002)).

Infection with human papillomaviruses (HPVs) is a factor that is associated with development of cervical cancer (e.g., zur Hausen, *Virology* 184:9-13 (1991); Stanley, *Best Prat. Res. Clin. Obstet. Gynaecol.* 15:663-676 (2001)). Therefore, the presence of molecules that inhibit or bind to HPV is useful for preventing both HPV infection and the development of cervical cancer. Exemplary anti-HPVs polypeptides include, e.g. neutralizing antibodies that bind HPV type 16 E6 or E7 protein (e.g. Mannhart et al., *Mol. Cell. Biol.* 20:6483-6495 (2000)), HPV-binding proteins, or HPV proteins that can be used to elicit an immune response directed to the virus.

Viral transmissions, like HIV, HSV, or HPV, involves mother to baby transmission, with vaginal delivery being one of transmission routes (Montgomery et al., *Lancet* 360:643-644 (2002); Brown et al, *JAMA* 289:203-209 (2003); Puranen et al., *Am. J. Obstet. Gynecol.* 174:694-699 (1996)). Therefore, expression of molecules that inhibit or bind to HIV, HSV or HPV in vaginal colonized lactobacilli is useful for reducing the load of infectious viral particles in infected women, as a means of restricting vertical transmission of the virus from the pregnant mothers to their newborns, during delivery.

The capacity to bind a pathogen such as a virus or bacteria may be conferred onto the bacteria of the invention in at least several ways. The first is by making the bacteria express on its surface the normal host receptor for the virus, such as ICAM-1 for human rhinovirus (HRV) (major group) and CD4 for HIV. These are normal human proteins and the complete sequences of many of these genes have been determined and are stored in the database GenBank.

A second method is by expressing on the bacterial surface an antibody fragment or other polypeptide that binds to a conserved determinant on the viral surface, such as VP4 on poliovirus, or gp120 on HIV. Antibody fragments (and peptides) specific for essentially any antigen can be selected, e.g., from a phage-display library (Marks et al., *J. Biol. Chem.* 267:16007-16010 (1992)). Antibodies can be directed to any epitope on or associated with a pathogen as well as other epitopes such as those discussed below.

A third method involves the expression of carbohydrate-binding polypeptides on the surface of the bacteria. Examples of these molecules include heparin-binding polypeptides, or mannose-binding polypeptides.

Anti-bacterial polypeptides include those that bind to or inhibit growth or colonization by uropathogenic *E. coli*. Exemplary anti-bacterial polypeptides include, e.g., permeability-increasing protein against gram-negative bacteria (Levy, *Expert Opin. Investig. Drugs* 11:159-167 (2002), mammalian ant-microbial peptides, β-defensins (Ganz & Lehrer, *Pharmacol. Ther.* 66:191-205 (1995), bacteriocins (e.g., Loeffler et al., *Science* 294:2170-2172 (2001) and antibodies that specifically bind to the bacteria.

Anti-fungal polypeptides include those that bind to or inhibit growth or colonization by fungi such as *Candida*.

Additional examples of biologically-active polypeptides useful according to the invention include therapeutic polypeptides or agents such as anti-inflammatory molecules, growth factors, molecules that bind to, or antagonize, growth factors, therapeutic enzymes, antibodies (including, e.g., antibody fragments or single-chain antibodies) and molecules that inhibit or treat cancer including cervical cancer. These examples are not intended to be limiting as numerous other therapeutically active polypeptides can readily be cited.

Anti-inflammatory molecules include, e.g., antibodies or other molecules that specifically bind to tumor necrosis factor (TNF) or interleukin-8 (IL-8). Other exemplary anti-inflammatory molecules include IL-10 and IL-11.

Growth factors useful in the invention include, e.g., those involved in local tissue repair such as keratinocyte growth factor (KGF), heparin-binding epidermal growth factor (HB-EGF), fibroblast growth factor (FGF) and transforming growth factor-beta (TGF-□, or antagonists of these molecules.

Therapeutic enzymes include, e.g., nitric oxide (NO) synthase.

Anti-cancer molecules include those that induce apoptosis, that regulate cell cycle such as p53, or that act as a vaccine to target cancer-specific epitopes.

Vaccine molecules useful in the invention include polypeptides that elicit an immune response to viruses, bacteria, or fungi. Exemplary viral vaccines elicit response to, e.g., HIV, HPV, HSV, or smallpox.

IV. Delivery

Delivery of engineered bacteria to a desired mucosal surface depends on the accessibility of the area and the local conditions. For example, engineered bacteria may be placed in a saline solution or in a foam for delivery onto the vaginal mucosa. Foams can include, e.g., one or more hydrophobically modified polysaccharides such as cellulosics and chitosans. Cellulosics include, for example, hydroxyethyl cellulose, hydroxypropyl cellulose, methyl cellulose, hydroxypropylmethyl cellulose, hydroxyethyl methyl cellulose, and the like. Chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, and the like. Foam can also include other components such as water, ethyl alcohol, isopropyl alcohol, glycerin, glycerol, propylene glycol, and sorbitol. Spermicides are optionally included in the bacterial composition. Further examples of foams and foam delivery vehicles are described in, e.g., U.S. Pat. Nos. 5,595,980 and 4,922,928.

Alternatively, the bacteria can be delivered as a suppository or pessary. See, e.g., U.S. Pat. No. 4,322,399. In some embodiments, the bacteria of the invention are prepared in a preservation matrix such as described in U.S. Pat. No. 6,468,526 and are delivered in a dissolvable element made of dissolvable polymer material and/or complex carbohydrate material selected for dissolving properties, such that it remains in substantially solid form before use, and dissolves due to human body temperatures and moisture during use to release the agent material in a desired timed release and dosage. See, e.g., U.S. Pat. No. 5,529,782. The bacteria can also be delivered in a sponge delivery vehicle such as described in U.S. Pat. No. 4,693,705.

In some embodiments, the bacteria are administered orally. For example, a daily dose of about $10^8$ lactobacilli can be used to restore the normal urogentital flora. See, e.g., Reid et al., *FEMS Immuno. Med. Microbiol.* 32, 37-41 (2001).

In some embodiments, applications of engineered bacteria to a mucosal surface will need to be repeated on a regular basis; optimal dosing intervals are routine to determine, but will vary with different mucosal environments and bacterial strain. The dosing intervals can vary from once daily to once every 2-4 weeks.

In embodiments where bacteriophage are introduced to transform native *Lactobacillus*, the nucleic acid of the selected bacteriophage may be manipulated such that the heterologous gene(s) replaces the genes coding for bacteriophage coat proteins, rendering the bacteriophage replication-defective. Adding these recombinant DNA molecules into cell lysates containing functional bacteriophage proteins will lead to assembly of functional bacteriophage particles carrying the heterologous gene(s). These replication-defective bacteriophage particles can then be introduced onto a desired mucosal surface to infect selected floral bacteria. The typical dosage would be $10^8$ to $10^{12}$ PFU/ml applied to the mucosal surface. The proportion of solution to the treated surface should approximate 0.1 to 1.0 ml per square centimeter of mucosal surface. The vehicle would be similar to the vehicle described above for the bacteria.

All publications and patent applications cited in this specification are herein incorporated by reference as if each individual publication or patent application were specifically and individually indicated to be incorporated by reference.

EXAMPLES

The following example is offered to illustrate, but not to limit, the claimed invention.

Introduction

The present invention involves the genetic modification of human isolates of *Lactobacillus jensenii* to express, secrete, or surface anchor biologically active polypeptides. To demonstrate this invention, high affinity HIV- or HSV-binding proteins were expressed in *Lactobacillus jensenii*. These recombinant bacteria are intended to be instilled into the vagina, where they will colonize the mucosa and produce virus-binding proteins that either remain associated with the cell-surface of these bacteria or are secreted into the surrounding mucosal biofilm matrix. Subsequent binding of the infectious viral particles to these proteins traps the virus and impedes its transmigration through the protective mucosal barrier. Since an increased residence time within the mucosa will expose the viral particles to virucidal substances (like lactic acid and peroxide), a significant population of the virus introduced into the vagina from the ejaculate of the infected male partner is likely to become inactivated when retained within this hostile environment. In this manner, the entire biofilm may be transformed into a more effective biological barrier, which serves as a protective shield against viral transmission to the female host.

Little, if any, of this work has been devoted toward the use of human vaginal isolates of lactobacilli as expression hosts. Indeed, as described herein, it was discovered by the inventors that some vaginal isolates (e.g., *L. crispatus*) could not be transformed, while *L. jensenii* could be efficiently transformed. The genetic modification of colonizing vaginal isolates of *L. jensenii* is described herein. These bacteria have been modified to express a prototypical HIV-binding protein, 2D-CD4. The 2D-CD4 molecules produced by these genetically modified bacteria exhibit potent biological activity, including the ability to bind to gp120 and to inhibit HIV infectivity in vitro. This work demonstrates the successful expression of a complex disulfide-bonded mammalian protein in a vagina-colonizing isolate of *Lactobacillus*. Furthermore, it enables the clinical efficacy of the engineered bacteria to block HIV transmission in women.

Experimental Methods

Bacterial strains and plasmids. Naturally occurring human vaginal isolates of *L. jensenii* and *L. crispatus* were obtained from vaginal swabs of healthy volunteers. Culture media for the routine propagation of *L. jensenii* and *L. crispatus* (37° C., 5% $CO_2$) included Mann Rogosa Sharpe (MRS) broth and Rogosa SL broth, and were obtained from Difco (Detroit, Mich.). Plasmids were introduced by electroporation into *L. jensenii* by the following method.

For plasmid selection and maintenance, erythromycin (20 μg/ml) was added to either liquid or solid media. For shuttle plasmid construction and maintenance, *E. coli* DH12s cells bearing the recombinant constructs were grown in LB broth (Difco) at 37° C., supplemented with ampicillin (100 μg/ml). *E. coli*-derived plasmids were transformed into *L. jensenii* using modifications of the protocol of Luchansky et al., *J. Dairy Sci.* 74:3293-3302 (1991). Briefly, freshly inoculated *L. jensenii* were cultured in MRS broth to 0.6-0.7 at $OD_{600}$ at 37° C. and 5% $CO_2$. The bacterial cells were harvested, washed and re-suspended in 952 mM sucrose and 3.5 mM $MgCl_2$ at 4° C. Using a pre-chilled 0.2 cm gap cuvette, competent cells were added to 1~2 μg of DNA and electroporated immediately at 2.5 kV/cm and 200 ohms using Gene Pulser II (Bio-Rad, Hercules, Calif.). Afterward, cells were allowed to recover in prewarmed MRS broth for two hours at 37° C., prior to being plated on selective MRS agar plate containing 20 μg/ml erythromycin.

Expression vector. The primary shuttle vector used in these studies was pOSEL144 (FIG. 1), a modified version of pLEM7 (Fons et al., *Plasmid.* 37:199-203 (1997)) in which a colE1 origin of replication was added from pBluescript at the Acc I site. The partial IS element was deleted by first cutting with Sma I, partially digesting with Nde I, blunting with Klenow fragment and then re-ligating. Finally, the plasmid was subjected to site-directed mutagenesis to remove two Mfe I sites within the erm gene, resulting in pOSEL175.

Cloning of S-layer Signal Sequence. S-layer signal sequence (CbsA$_{ss}$) of *L. crispatus* of human vaginal isolates was cloned to target for protein secretion in *Lactobacillus*. The S-layer gene (cbsA) was amplified from chromosomal DNA isolated from a proprietary Xna strain of *L. crispatus* using primers designed to flank the sequence of the cbsA gene from *L. crispatus* JCM5810 (Martinez et al., *J. Bacteriol.* 182:6857-6861 (2000)). Two primers, 5'-GC GAATTCA AGG AGG AAA AGA CCA CAT-3' (SEQ ID NO:12) and 5'-CCA GCTAGC TGA AAC AGT AGA AAC GGC-3' (SEQ ID NO:13), were designed to amplify the cbsA sequence from the putative ribosome binding site to the signal peptidase cleavage site, with EcoRI and NheI sites added to the 5' and 3' ends, respectively. The amplified CbsA$_{ss}$ was then digested and used for cloning in the expression cassette.

Construction of expression cassettes in *L. jensenii*. Oligonucleotide primers for PCR amplification of various portions of the fusion constructs detailed in this study include the following:

| | | |
|---|---|---|
| P$_{59}$.f | 5'-GGCGAGCTCCCCAAAGAAGCGCGTAATATC-3' | (SEQ ID NO:6) |
| P$_{59}$.r | 5'-GGAAACACGCTAGCACTAACTTCATT-3' | (SEQ ID NO:7) |
| P$_{23}$.f | 5'-GTGGAGCTCCCCGAAAAGCCCTGACAACCC-3' | (SEQ ID NO:8) |
| P$_{23}$.r | 5'-GGAAACACGCTAGCACTAACTTCATT-3' | (SEQ ID NO:9) |
| 2D-CD4.f | 5'-GCGGCTAGCAAGAAAGTTGTTTTAGGTAAA-3' | (SEQ ID NO:10) |
| 2D-CD4.r | 5'-GCACAATTGTGATGCCTTTTGAAAAGCTAA-3' | (SEQ ID NO:11) |
| CbsAss.f | 5'-GCGAATTCAAGGAGGAAAAGACCACAT-3' | (SEQ ID NO:12) |
| CbsAss.r | 5'-CCAGCTAGCTGAAACAGTAGAAACGGC-3' | (SEQ ID NO:13) |
| HveC V & γ.f | 5'-GGCGCTAGCCAGGTGGTCCAGGTGAACGACTCC-3' | (SEQ ID NO:14) |
| HveC V.r | 5'-CCGCAATTGCATCACCGTGAGATTGAGCTGGCT-3' | (SEQ ID NO:15) |
| HveC γ.r | 5'-GCGCAATTGGAACATCCTAGCTCTTGTCCT-3' | (SEQ ID NO:16) |

The promoters used in the study were P$_{23}$ and P$_{59}$ from *Lactococcus lactis* (van der Vossen et al., *Appl. Environ. Microbiol.* 53:2452-2457 (1987)). The first 183 residues comprising the N-terminal two extracellular domains of human CD4 (2D-CD4) were recoded by assembly PCR (Stemmer et al., *Gene* 164:49-53 (1995)) to conform to a preferred *Lactobacillus* codon usage. The DNA sequence encoding for cyanovirin-N (Boyd et al., *Antimicrob. Agents Chemother.* 41:1521-1530 (1997)) was also synthesized by assembly PCR. The DNA sequence encoding HveC-V (Krummenacher et al., *J. Virol.* 73:8127-8137 (1999)) was obtained by PCR amplification of a human cDNA library whereas the DNA sequence encoding a secreted form of HveC-γ (Lopez et al., *J. Virol.* 75:5684-5691 (2001)) was obtained by PCR amplification of a human cDNA clone encoding this protein (IMAGE clone #143177). All expression constructs were confirmed by DNA sequence analysis.

Analysis of heterologous protein expression in *L. jensenii*. The recombinant *L. jensenii* cells were grown (37° C. and 5% $CO_2$) in Rogosa broth that was buffered with 100 mM HEPES (pH 7.4). The cell cultures were grown to various densities and then the bacteria were removed by centrifugation (3,800×g, 15 m). The supernatants were transferred to a fresh container and the proteins secreted into this spent medium were then precipitated by the addition of ice-cold trichloroacetic acid (TCA) at a final concentration of 20%. The protein precipitates were washed with 70% ethanol, air-dried and heat denatured in SDS-PAGE loading buffer (50 mM Tris-HCl, pH 6.8, 0.4% SDS, 6% sucrose, 0.01% bromophenol blue), either with or without dithiothreitol (10 mM). To estimate the relative amounts of cell-surface-associated proteins in *L. jensenii*, bacterial cells were extracted at room temperature for 15 minutes with SDS-PAGE loading buffer. The extracted proteins were separated from insoluble debris by centrifugation 14,000×g for 5 minutes, and then resolved by SDS-PAGE using a 4-12% NuPAGE system (Invitrogen). For Western analysis, proteins were electrotransferred on to PVDF membranes (Millipore) according to the manufacturer's directions. The membrane was probed with polyclonal rabbit anti-CD4 antibodies T4-4 (AIDS Research and Reference Reagent Program of the National Institute of Health) or with rabbit anti-M6 of *S. pyogenes*, or rabbit anti-cyanovirin antibodies and then visualized by using alkaline phosphatase (AP)-conjugated anti-rabbit IgG (Sigma) and chromogenic detection reagents (Promega). Alternatively, the antigen-antibody reaction was visualized by using enhanced chemiluminescent reagents (Amersham Biosciences).

Partial purification of *Lactobacillus*-derived 2D-CD4. Culture supernatants were treated with protease inhibitor cocktail (Roche Applied Science), dialyzed against 50 mM sodium phosphate, pH 6.8 at 4° C. in 10-kDa cut-off dialysis membrane and then passed over a column of Q Sepharose Fast Flow resin (Amersham Biosciences). The 2D-CD4 proteins in the flow through were then bound to SP Sepharose Fast Flow (Amersham Biosciences) and eluted in the buffer containing 0.8 M NaCl. The amount of eluted 2D-CD4 was determined by Western blot and activity analyzed by CD4 ELISA and gp120 binding using soluble CD4 (AIDS Research and Reference Reagent Program of the National Institutes of Health) as a standard. The isolated soluble proteins were also subjected to N-terminal amino acid sequencing at Molecular Structure Facility, University of California-Davis.

CD4 ELISA and gp120 binding assays. The concentration of correctly folded 2D-CD4 protein was assessed by a CD4-capture ELISA in a 96 well microtiter plate format. The 2D-CD4 proteins secreted by *L. jensenii* were captured by the CD4-specific monoclonal antibody Sim.4 (McCallus et al. *Viral Immunol.* 5:163-720) at 10 ng/ml. The bound CD4 molecules were detected with a polyclonal rabbit antibody, T4-4 (AIDS Research and Reference Reagent Program), which was visualized by incubation with AP-conjugated anti-rabbit IgG (Sigma) and the AMPAK ELISA amplification system (Dako Diagnostics, Inc.). The gp120 binding activity of 2D-CD4 was performed essentially as described by Moore, *AIDS Res. Hum. Retroviruses* 9: 209-219 (1993) with minor modification. Briefly, 96 well microtiter plates coated with a polyclonal sheep anti-gp120 antibody, D7324 (Aalto Bio Reagents, Dublin, Ireland), were blocked (TBS, 2% non-fat dry milk) and incubated with 10 ng/well recombinant gp120 (rgp120, Protein Sciences Corp.). Samples containing CD4 molecules were then captured by rgp120, and bound CD4 molecules were detected using the polyclonal rabbit antibody, T4-4, as described above. The biological activity of *Lactobacillus*-derived cyanovirin was also determined by gp120 binding assay. Samples containing cyanovirin were first capatured by rgp120, and bound cyanovirin molecules were then detected using polyclonal rabbit anti-cyanovirin antibody.

HIV-1 infectivity assay. The effect of 2D-CD4 proteins secreted from *L. jensenii* on HIV-1 entry was determined by using a single-cycle infection assay (Connor et al., *J. Exp. Med.* 185:621-628 (1997); Chen et al., *J. Virol.* 68:654-60. (1994)). Reporter viruses expressing luciferase (HIV-1$_{HxB2}$ strain Env) were produced by co-transfecting HEK293T cells with plasmids encoding the envelope-deficient HIV-1 NL4-3 virus, the pNL-Luc plasmid carrying the luciferase reporter gene, and the pSV plasmid expressing the glycoproteins from HIV-1$_{HxB2}$ strain. The supernatant was collected 48 hours after transfection and filtered. Virus stocks were analyzed for HIV-1 p24 antigen concentration by ELISA. Subsequently, the virus p24 antigen concentration in virus-containing supernatant was determined by p24 antigen ELISA.

One day before infection, HeLa-CD4 cells expressing CXCR4 were seeded at 5×10$^4$ cells per well in a 48-well tissue culture plate. Env-pseudotyped, luciferase-expressing reporter HIV-1$_{HxB2}$ viruses were first incubated with different concentrations of 2D-CD4 protein (37° C., 30 minutes), either directly from culture supernatants or prepared after partial purification. Subsequently, the virus in the reaction mixtures was used to infect cells (37° C., 1 hr). Unbound virus was removed by washing with PBS. Alternatively, *L. jensenii* bacteria, resuspended at 2.5 or 5×10$^8$ cells/ml, were cultured in Medium 199 (37° C., 30 minutes). Then, the bacteria, along with input viruses, were added to HeLa cells expressing CD4-CXCR4 (37° C., 1 hour). Subsequently, cells were cultured in Dulbecco's modified Eagle's medium supplemented with 10% FBS at (37° C., 48 hours, 5% CO$_2$). The cells were washed once with PBS and lysed with reporter lysis buffer (Promega Corp. Madison, Wis.). Luciferase activity in a mixture of luciferase substrate and cell lysate was measured in relative light units (RLU) with a Chiron microplate luminometer.

Results:

The human vaginal ecosystem harbors a complex microflora. Lactobacilli are dominant within the microflora of healthy American and European women, and have been shown to adhere tightly to vaginal epithelial cells in vitro. Most healthy women are predominantly colonized by either *L. crispatus* or *L. jensenii* relative to other *Lactobacillus* species. Thus, *L. crispatus* and *L. jensenii* were the two species of *Lactobacillus* selected for analyzing in vitro growth properties, colonization, endogenous plasmid profiles, antibiotic susceptibility, relative transformation efficiency, and level of functional protein expression.

Growth properties: *L. jensenii* strains were isolated from vaginal swabs of healthy individuals. These isolates are useful in the identification of various phenotypic traits (e.g. lactic acid production, autoaggregation and adherence to vaginal epithelial cells) that will be necessary to maintain in the final engineered product. For comparison, reference strains of various vaginal *Lactobacillus* isolates, including *L. crispatus*, *L. jensenii*, *L. gasseri*, *L. fornicalis* and *L. vaginalis*, were obtained from the American Type Culture Collection.

Antibiotic susceptibility/plasmid profiles: Environmental (WT) isolates of bacteria frequently contain transmissible genetic elements (plasmids, transposons, and temperate bacteriophage) that confer a genetic advantage for viability in vivo. The presence of naturally occurring plasmids or integrated transposons, however, could adversely affect the stability of plasmid based expression constructs used in our preliminary studies, either interfering with replication or with the ability to use antibiotic selection. Alternatively, any naturally occurring plasmid isolated from WT *L. jensenii* could potentially be engineered for heterologous protein production without the necessity of antibiotic selection. Susceptibility testing was used to determine the range of sensitivity of WT isolates of *L. jensenii* and *L. crispatus* to various antibiotic compounds with defined modes of action. Any strains of *L. jensenii* that were found to be resistant to specific compounds were examined more thoroughly for plasmids and transposons that commonly contain resistance genes. Both disc diffusion and broth microdilution assays (in MRS) were used to assess antibiotic susceptibility. All strains tested were sensitive to erythromycin (<0.5 µg/ml) and moderately sensitive to tetracycline (4 µg/ml). Most of the strains were sensitive to oxacillin (<0.5 µg/ml) with the exception of two strains that appeared highly resistant (>128 µg/ml). All strains were found resistant (>128 µg/ml) to aminoglycosides (kanamycin, gentamycin), which is expected for aerotolerant bacteria that do not synthesize respiratory quinones.

Optimization of electroporation in *Lactobacillus*: To support cloning and heterologous protein expression in these vaginal *Lactobacillus* strains, electroporation methods were developed for application to *L. jensenii* and *L. crispatus*. Various parameters, including culture media, cell growth stages, DNA concentration, wash or electroporation buffer composition, cuvette gap size, and voltage were evaluated to determine conditions that improved transformation frequencies for the WT *Lactobacillus* strains in our collection. *E. coli*-derived plasmids were transformed into *L. jensenii* by electroporation according to Luchansky et al. (*J. Dairy Sci.* 74:3293-302 (1991)) with modifications. Briefly, freshly inoculated *L. jensenii* were cultured in MRS broth to 0.6-0.7 at OD$_{600}$ at 37° C. and 5% CO$_2$. The bacterial cells were harvested, washed and re-suspended in 952 mM sucrose and 3.5 mM MgCl$_2$ at 4° C. Using a pre-chilled 0.2 cm gap cuvette, competent cells were added with 1~2 µg of plasmid DNA (e.g. pOSEL175) and electroporated immediately at 2.5 kV/cm and 200 ohms using Gene Pulser II (Bio-Rad, Hercules, Calif.). Afterward, cells were allowed to recover in prewarmed MRS broth for two hours at 37° C., prior to being plated on selective MRS agar plate containing 20 µg/ml erythromycin.

In contrast to transformations of *L. jensenii*, clinical isolates of *L. crispatus* were not successfully transformed in spite of diligent efforts to do so. The following table lists the protocols and success rates achieved for *L. jensenii* and *L. crispatus*. Protocols fused for attempts to transform *L. crispatus* included parameters described in: Luchansky et al. (*J. Dairy Sci.* 74:3293-302 (1991); Maassen, *J. Immunol. Methods* 223:131-136 (1999) (including two washes of cells in distilled H$_2$O, one wash in 30% (w/v) PEG-1000 followed by electroporation at (8500V/cm$^2$) in 30% PEG-1000, 100 Ω, 25 mF capacitance); and Bhowmik & Steele, *J. Gen. Microbiol.* 139:1433-1439 (1993) (involving bacteria grown in MRS broth plus 1% glycine, wash four times in buffer (0.5 M sucrose, 0.1 mM HEPES, pH 7.0) and electroporation in same buffer, 0.4 cm cuvette, 2.5 kV, 25 µF, 200 Ω). To date, human vaginal isolates of *L. crispatus* could not be transformed under any conditions tested.

| Bacteria | Protocols | Transformants (CFU/µg plasmid DNA) |
|---|---|---|
| *L. jensenii* 1153 | Electroporation | 5 × 10$^3$ |
| *L. jensenii* Xna | Electroporation | 1-1.5 × 10$^3$ |
| All available *L. crispatus* clinical strains including: Xna, 1160, 2116, 2059, 6061, and 6090 | Various protocols and combinations thereof including: Different buffers, varied electroporation parameters, different growth conditions, different plasmid replication origins, different plasmid antibiotic resistance markers, and prolonged duration of cell recovery after electroporation. Protocols included heat shock of bacteria to inactivate host restriction systems as well as removal of S-layer with chaotropic salts prior to competent cell preparation. | 0 in all cases |

Development of expression vectors in *Lactobacillus*: Plasmid vectors for expression of proteins in *Lactobacillus* were engineered, based on a cloning vector (pLEM7) modified from an endogenous plasmid of *L. reuteri* LEM3 (Fons et al., *Plasmid* 37:199-203 (2002)). One of these such vectors, pOSEL144, contains a multiple cloning site, an origin for replication in *E. coli* (colE1), an additional origin for replication in *Lactobacillus* (repA) and an erythromycin resistance marker (erm) for positive selection of the plasmid in both *E. coli* and *Lactobacillus* (FIG. 1).

A modular cloning approach to facilitate the cloning and expression of heterologous polypeptides such as HIV-binding ligands. Using different combinations of expression strategies, these molecules are designed either to be secreted into the extracellular space (i.e. the surrounding media), or to be retained as a surface expressed protein linked by a natural covalent modification to the bacterial cell wall (peptidoglycan). The cassettes can contain four components, including promoter elements, signal peptide, virus-binding ligand, and anchor sequences (FIG. 1). For the expression of various ligands, unique restriction sites were placed between each module for easy one-step cloning.

To obtain proof of whether this modular approach would work, several signal sequences and anchoring sequences were analyzed to determine the expression of biologically active CD4 protein fusions expressed under the control of either the P$_{23}$ or the P$_{59}$ promoter. In addition to utilizing the M6 protein signal sequence from *S. pyogenes*, the signal sequences of the α-Amylase (Amy) gene (amyA) from *L. amylovorus* and the S-layer gene (cbsA) from *L. crispatus* were cloned. Both sequences were obtained by PCR from chromosomal DNA isolated from either *L. amylovorus* or *L. crispatus*, and were designed to contain a ribosomal binding site and span the N-terminal sequence of either gene up to the signal peptidase cleavage site. The Amy signal sequence (Amy$_{ss}$) was: MKKKKSFWLVSFLVIVASVFFISFGFS-NHSKQVAQA (SEQ ID NO:3). The CbsA signal sequence (CbsA$_{ss}$) was: MKKNLRIVSAAAAALLAVATVSA (SEQ ID NO:2). Unique restriction endonuclease sites were added to the ends of the primers so that any potential ligand protein could be cloned in frame with either signal sequence. The amplified cassettes, containing either CbsA$_{ss}$ or Amy$_{ss}$, were then digested and cloned into the modular system.

Secretion of heterologous proteins (e.g., 2D-CD4) by modified *L. jensenii* relies on the Sec machinery that mediates translocation of a precursor protein across the membrane. The 2D-CD4 protein is first synthesized as signal sequence (e.g., CbsAss) bearing precursor. Upon translocation across the membrane, the CbsAss is cleaved by signal peptidase, thus releasing the mature 2D-CD4 into the extracellular milieu. The N-terminal amino acid sequences of secreted proteins are consistent with the predicted sequences of mature protein.

To express CD4 on the surface of *L. jensenii*, two cell-wall anchors were used from either the M6 protein (emm6) of *S. pyogenes* or the PrtP protease of *L. paracasei*. Unlike the M6 protein, which has a signature LPXTG (SEQ ID NO:17) cell wall sorting signal, the sortase motif for PrtP is LPKTA (SEQ ID NO:18). The PrtP anchor was prepared by PCR amplification from *L. paracasei* ATCC 25302, then cloned and confirmed by DNA sequence analysis.

The first two extracellular domains (K$^1$-S$^{183}$) of human CD4 (2D-CD4) were chosen for surface expression. 2D-CD4 is capable of high-affinity binding to gp120 as is the 4-domain sCD4. Because differences in codon bias affect protein expression in *L. jensenii*, the cDNA clone of human 2D-CD4 was re-coded to conform more closely to the optimal *Lactobacillus* codon usage. The 2D-CD4 sequence containing Nhe I site at its 5' end and Mfe I site at its 3' end was amplified from recoded CD4 sequence. The resulting PCR product was cut by Nhe I and Mfe I, and ligated with Nhe I/Mfe I-treated vector for surface expression of 2D-CD4. The nucleotide sequences of the constructs were verified prior to transformation into *L. jensenii*.

Surface anchoring of 2D-CD4 in *L. jensenii*: To determine the extent of surface expression of 2D-CD4, a set of constructs harboring different surface anchors were analyzed along with pOSEL144, which was used as a negative control. Proteins from modified bacteria were fractionated into cell-, cell wall-, and protoplast-associated pools. 2D-CD4 was detected under P$_{59}$ promoter control in the cell-wall associated and protoplast fractions, whereas it was undetectable in cell wall fractions in constructs harboring the P$_{23}$ promoter with either M6 or CWA100 as cell wall anchors, where CWA100 represents a cell wall anchoring domain of 100 amino acids in length of *S. pyogenes*. This lack of detectable cell wall associated 2D-CD4 was not due to protein instability during cell wall digestion. The inefficient surface anchoring of 2D-CD4 driven by cell wall sorting signal either from M6 of *S. pyogenes* or PrtP protease of *L. paracasei* necessitated identification and use of native cell wall sorting signals in *L. jensenii*.

Secretion of biologically active 2D-CD4: An analysis of surface-anchored constructs demonstrated that a majority of 2D-CD4 was released into the culture medium. Furthermore, in vitro binding studies showed that some soluble two- or four-domain CD4 molecules did not diffuse freely in biological fluids, but rather became cell-surface associated. The growth and adherence properties of CD4-expressing lactobacilli appear similar to those of wild-type strains, suggesting that the expression of these virus-binding proteins will not interfere with the ability of the engineered *Lactobacillus* to colonize the human host. Thus an engineered *Lactobacillus* expressing these CD4 molecules could maintain a high local concentration of the molecule without the explicit need for covalent attachment to the peptidoglycan.

Figure 2:
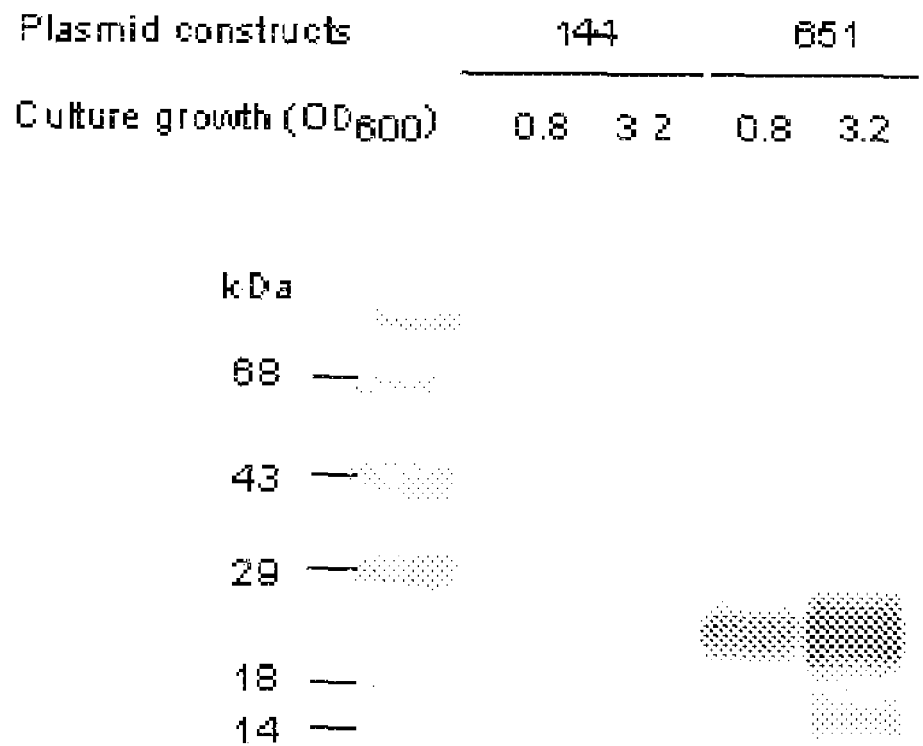
FIG. 2 illustrates results from Western analysis of release of 2D-CD4 by *L. jensenii* Xna harboring the 2D-CD4 expression plasmid pOSEL651 (Xna-651) relative to the control plasmid pOSEL144 (Xna-144). Samples were collected either at optical density at 600 nm ($OD_{600}$) 0.8 or 3.2. Proteins were collected by precipitation with TCA from culture supernatants from corresponding bacterial cells and subjected to electrophoretic separation under reducing SDS-PAGE for Western blot analysis with polyclonal anti-CD4 antibodies, T4-4. The pOSEL651 construct contained the following elements: $P_{23}$ promoter-CbsAss-2D-CD4.
Figure 3:
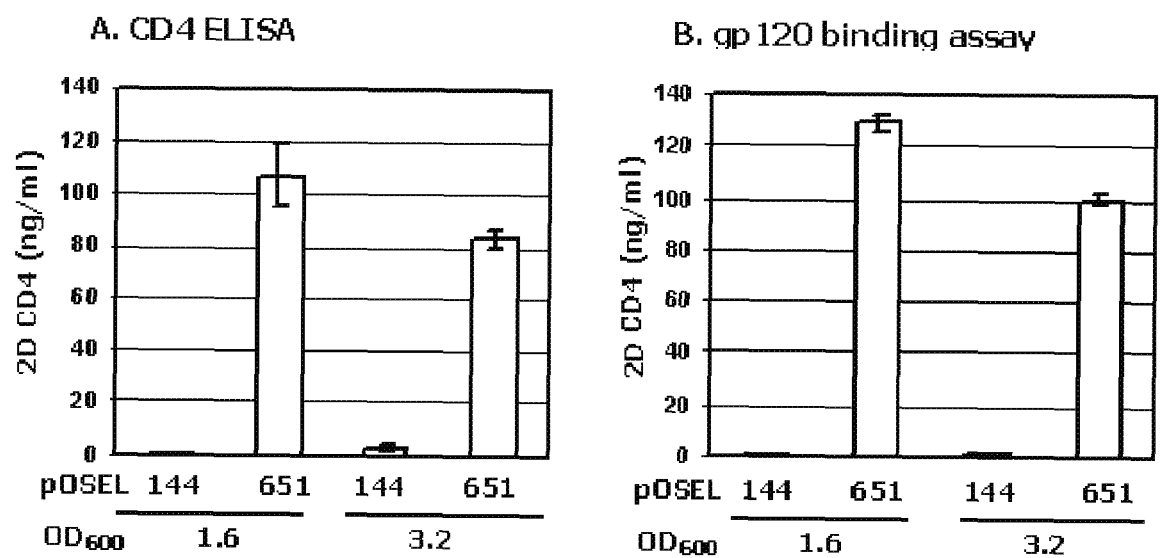
FIG. 3 illustrates that the engineered *L. jensenii* Xna secretes biologically active 2D-CD4. *L. jensenii* Xna-144 or Xna-651 bacteria were grown in MRS broth (37° C. and 5% $CO_2$). Culture supernatants were used for CD4 ELISA (A) and gp120 binding assay (B). 2D-CD4 concentrations were determined from standard curves generated with refolded 2D-CD4 expressed in *E. coli*.

In the cassette-based expression system, the anchor domain determines whether the expressed virus binding proteins are surface-anchored or secreted. To generate secreted forms of the HIV-binding proteins, a stop codon was introduced in the N-terminal region of the cell wall anchoring domain. A series of plasmids designed for protein secretion with the following components were constructed: $P_{23}$ promoter-signal sequence of *S. pyogenes* M6 (M6ss)-$M6_{120}$-2D-CD4 (pOSEL128); $P_{59}$ promoter-M6ss-$M6_{120}$-2D-CD4 (pOSEL197); and $P_{23}$ promoter-CbsAss-2D-CD4 (pOSEL651), where $M6_{120}$ represents the N-terminal 120 amino acid residues of *S. pyogenes* M6. Both modest and high levels of recombinant 2D-CD4 production were achieved in *L. jensenii* 1153 and Xna transformed with pOSEL128, 197, or 651 when grown to log phase. The expressed protein continued to accumulate, even as the pH of the culture medium became acidified after overnight incubation. FIG. 2 showed a time-dependent release of 2D-CD4 by *L. jensenii* Xna harboring pOSEL651 relative to the bacteria harboring control plasmid pOSEL144. To characterize the biological activity of the secreted 2D-CD4 protein, CD4 ELISA and gp120 binding assays were performed. The CD4 ELISA was developed to determine the presence of correctly folded CD4 molecules captured onto a solid phase by adsorbed antibodies Leu3a or Sim.4. CD4 hybridoma (Sim.4) and CD4 monoclonal (Sim.4) are available at NIH AIDS Research and Reference Reagent Program. The Leu3a mAb is available at Becton Dickinson. Both antibodies recognized domain 1 of CD4, overlapping the gp120 binding site. Polyclonal antibodies against CD4 (T4-4) were used to detect bound CD4 molecules. Approximately 100 ng/ml of either $M6_{120}$-2D-CD4 or 2D-CD4 was detectable in the spent supernatant (FIG. 3). The gp120-binding activities of secreted $M6_{120}$-2D-CD4 or 2D-CD4 proteins correlated well with the results from CD4 ELISA (FIG. 3). Thus, 2D-CD4 is expressed in a native conformation based on its immuno-reactivity with the conformational dependent antibody Sim.4 and ability to bind the counter-ligand gp120.

*L. jensenii* derived 2D-CD4 inhibited HIV-1 infectivity in vitro. Several different approaches were used to determine whether 2D-CD4 secreted from strain Xna-651 interfered with the ability of an HIV-$1_{HXB2}$ virus, carrying a luciferase reporter, to infect HeLa cells expressing CD4-CXCR4 in a single cycle viral entry format.

Figure 4:
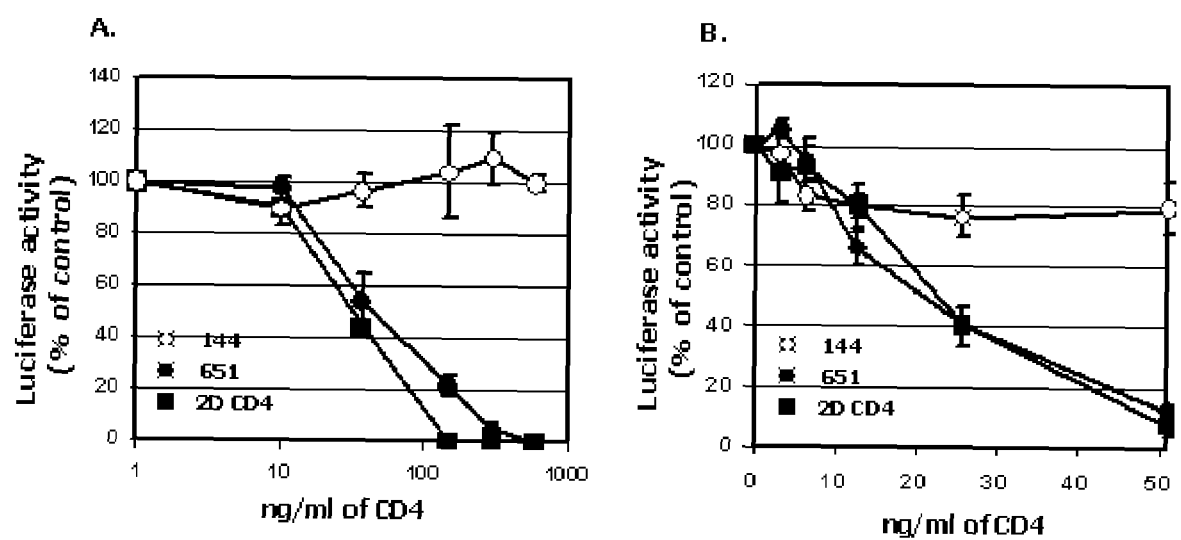
FIG. 4 illustrates that *L. jensenii* derived 2D-CD4 inhibits HIV-1 infectivity. The inhibitory effect of the 2D-CD4 protein produced by Xna-651 after partial purification (A) and conditioned medium 199 containing 2D-CD4 (B) on HIV-1 infectivity of HeLa cells expressing CD4-CXCR4 was determined by viral entry assay. The results (mean±SD) from triplicate determinations in a single experiment were presented and confirmed in a series of independent experiments. The luciferase activity from virus infected cells without addition of 2D-CD4 samples was defined as 100%. This corresponded to relative light units (RLU) values of 276±21 in panel A, 350±19 in panel B.

First, soluble 2D-CD4 secreted into the culture supernatant, by *L. jensenii* (pOSEL651), was partially purified using ion-exchange chromatography. As a positive control, biologically active 2D-CD4 proteins were added to samples prepared from the control strain (pOSEL144). Similar to the positive control, samples from *L. jensenii* (pOSEL651) inhibited HIV-1 infectivity in a dose-dependent manner, whereas samples prepared from the control strain (pOSEL144) had no apparent effect (FIG. 4).

Second, conditioned media was prepared by incubating *L. jensenii* at log phase in a HeLa cells compatible medium, Medium 199. Based on both CD4 ELISA and HIV-1 gp120 binding analysis, biologically active 2D-CD4 at 50 ng/5×10$^8$ colony-forming unit (CFU)/ml was routinely detected in the conditioned supernatant of *L. jensenii* (pOSEL651). Addition of this conditioned media to HeLa-CD4 cells inhibited HIV-1 infectivity in a dose-dependent manner. Once again, inhibitory concentrations of *L. jensenii*-derived 2D-CD4 were similar to those of an added 2D-CD4 control standard, while the conditioned media from *L. jensenii* (pOSEL144) was inactive (FIG. 4).

Figure 5:
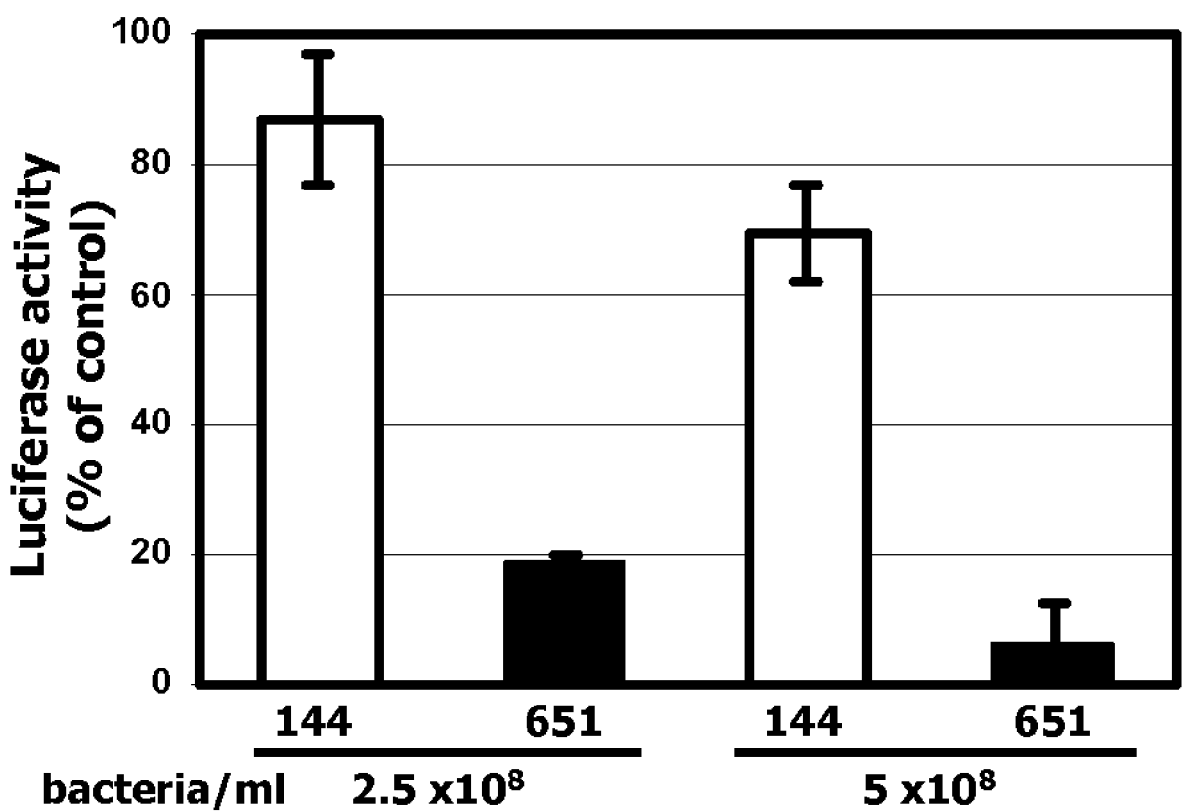
FIG. 5 illustrates that co-incubation of *L. jensenii* Xna-651 bacteria with HeLa-CD4 cells and recombinant viruses inhibit HIV-1 infectivity. *L. jensenii* Xna-144 or Xna-651 bacteria in medium 199 were co-incubated with Env-pseudotyped HIV-1$_{HxB2}$ and HeLa-CD4-CXCR4, for 1 hr at 37° C. in the viral entry assay. The results (mean±SD) from triplicate determinations in a single experiment were presented and confirmed in a separate experiment. The values presented represent luciferase activity relative to that derived from cells not treated with samples, which was defined as 100%. This corresponded to absolute RLU values of 324±19.

Co-incubation of *L. jensenii* Xna-651 bacteria with recombinant virus inhibited HIV-1 viral entry of target cells in vitro. In a separate set of studies, experiments were performed to evaluate whether co-incubation of *L. jensenii* Xna-651 with HeLa cells expressing CD4-CXCR4 and recombinant virus could decrease HIV-1 infectivity (FIG. 5). *L. jensenii* Xna-651 were pre-incubated in medium 199 and then added along with recombinant virus to HeLa cells expressing CD4-CXCR4 cells. A determination of virus-associated luciferase activity at 48 hours post infection revealed that the *L. jensenii* Xna-651 strain had a significant inhibitory effect on HIV-1 entry, whereas the control strain Xna-144 did not. *L. jensenii* Xna-651 inhibited HIV-1 entry by 79% (P<0.01) at cell density of $2.5\times10^8$/ml or by 90% (P<0.01) at cell density of $5\times10^8$/ml, relative to *L. jensenii* Xna-144. Similar results were observed when bacteria and viruses were added to cultured cells without pre-incubation of the bacteria in medium 199. Taken together, these results demonstrate clearly that a vaginally colonizing isolate of *L. jensenii*, engineered to express 2D-CD4, markedly inhibits the infection of cultured cells by a recombinant HIV-1 virus, thereby providing an in vitro demonstration of this anti-infective strategy.

Expression of cyanovirin-N in *L. jensenii*. To further demonstrate the versatility of the expression system, the 2D CD4 coding sequence in plasmid pOSEL651 was removed and replaced with the structural gene encoding cyanovirin-N, resulting in pOSEL647. To determine if the *L. jensenii* 1153 or Xna harboring pOSEL647 secrete any cyanovirin, proteins in conditioned media at different stages of growth were TCA precipitated, washed with ethanol, and resolved using a 4-12% reducing SDS-PAGE. Western blot analysis using polyclonal anti-cyanovirin antibodies detected modest level of *Lactobacillus*-derived cyanovirin at the predicted sizes. Furthermore, the secreted cyanovirin bound HIV-1 gp120, suggesting that the expressed proteins are to a large extent properly folded into their native conformation.

Expression of HveC in *L. jensenii*. The human herpesvirus entry mediator C (HveC) is a member of the immunoglobulin family used as a cellular receptor by HSV (e.g. Geraghty et al., *Science* 280:1618-1620 (1998)) and its gD binding domain located within the V-domain of HveC (e.g. Krummenacher et al., *J. Virol.* 73:8127-8137 (1999)). Point mutations within the V domain of HveC have been shown to eliminate glycoprotein D binding and, accordingly, impair entry activity for both HSV-1 and HSV-2 (Martinez & Spear, *J. Virol.* 76:7255-7262). In addition, a natural soluble isoform, designated HveCγ, also modulates susceptibility of host cells to HSV infection (e.g. Lopez et al., *J. Virol.* 75:5684-5691 (2001)). To secrete HveC in fusion with M6$_{120}$ in *L. jensenii* 1153, HveC expression plasmids were constructed under control of P$_{59}$ promoter and CbsAss. These plasmids included pOSEL215, designed for secretion of M6$_{120}$-HveC V-domain, pOSEL220 for secretion of M6$_{120}$-HveCγ and a control plasmid, pOSEL175. All of these plasmids were introduced into *L. jensenii* 1153 by electroporation. To determine if these bacterial strains secrete any HveC, proteins in conditioned media at different stages of growth were TCA precipitated, washed with ethanol, and resolved using a 4-12% reducing SDS-PAGE.

Figure 6:
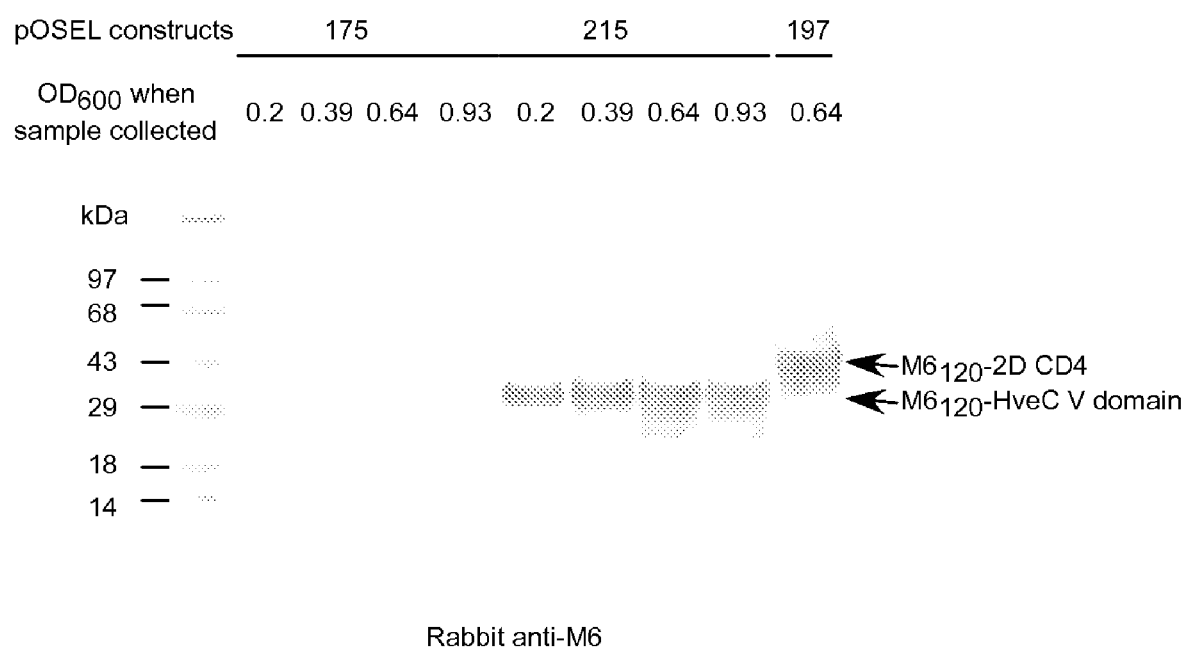
FIG. 6 illustrates secretion of $M6_{120}$-HveC V domain by modified *L. jensenii* 1153. Bacterial cells transformed with pOSEL175, 215, and 197 were grown in Rogosa SL broth. Proteins in cell-free conditioned media were TCA precipitated for Western analysis and reacted with a polyclonal M6 antiserum. The expression constructs contained the following elements: $P_{59}$ promoter-CbsAss-$M6_{120}$-HveC V in pOSEL215; $P_{59}$ promoter-CbsAss-$M6_{120}$-2D-CD4 in pOSEL197. $M6_{120}$ represents the N-terminal domain of *S. pyogenes* M6.

Western blot analysis using polyclonal anti-M6 antibodies and anti-HveC detected modest level of both M6$_{120}$-HveC V domain (FIG. 6) and M6$_{120}$-HveCγ at the predicted sizes. In addition, the ability of the M6$_{120}$-HveC V domain to react with mAb R1.302 was analyzed in western blot format, following Tris-Glycine PAGE (e.g. Krummenacher et al., *J. Virol.* 73:8127-8137 (1999)). M6$_{120}$-HveC bound to mAb R1.302 (which recognizes a conformationally dependent epitope within the V-domain), demonstrating the secreted M6120-HveC V protein adopts a native conformation.

The above example is provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A *Lactobacillus jensenii* bacterium recombinantly altered to express a biologically active protein, wherein the biologically active protein binds to a pathogen when the biologically active protein is contacted with a pathogen.

2. The bacterium of claim 1, wherein the protein requires a disulfide bond to be biologically active.

3. The bacterium of claim 1, wherein the biologically active protein is secreted.

4. The bacterium of claim 1, wherein the biologically active protein is on the bacterial surface.

5. The bacterium of claim 1, wherein the pathogen is a viral pathogen.

6. The bacterium of claim 5, wherein the viral pathogen is HIV.

7. The bacterium of claim 5, wherein the viral pathogen is HSV.

8. The bacterium of claim 6, wherein the biologically active protein is CD4 or an HIV-binding fragment of CD4.

9. The bacterium of claim 8, wherein the biologically active protein is 2D-CD4.

10. The bacterium of claim 1, wherein the biologically active protein is cyanovirin-N or a virus-binding fragment of cyanovirin-N.

11. The bacterium of claim 1, wherein the biologically active protein is HveC or a virus-binding fragment of HveC.

12. The bacterium of claim 1, wherein the biologically active protein is a therapeutic polypeptide.

* * * * *

SEQUENCE LISTING

```
<160> NUMBER OF SEQ ID NOS: 18

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence:signal
      sequence from S-layer gene cbsA (CbsA-ss) of Lactobacillus
      crispatus

<400> SEQUENCE: 1

Met Lys Lys Asn Leu Arg Ile Val Ser Ala Ala Ala Ala Ala Leu Leu
 1               5                  10                  15

Ala Val Ala Pro Val Ala Ala
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence:signal
      sequence from S-layer gene cbsA (CbsA-ss) of Lactobacillus
      crispatus

<400> SEQUENCE: 2

Met Lys Lys Asn Leu Arg Ile Val Ser Ala Ala Ala Ala Ala Leu Leu
 1               5                  10                  15

Ala Val Ala Thr Val Ser Ala
            20

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence:signal
      sequence from alpha-amylase (Amy) gene amyA (Amy-ss) of
      Lactobacillus amylovorus

<400> SEQUENCE: 3

Met Lys Lys Lys Lys Ser Phe Trp Leu Val Ser Phe Leu Val Ile Val
 1               5                  10                  15

Ala Ser Val Phe Phe Ile Ser Phe Gly Phe Ser Asn His Ser Lys Gln
            20                  25                  30

Val Ala Gln Ala
        35
```

```
<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence:anchor
      sequence

<400> SEQUENCE: 4

Val Thr Arg Thr Ile Asn Val Val Asp Pro Ile Thr Gly Lys Ile Ser
 1               5                  10                  15

Thr Ser Val Gln Thr Ala Lys Phe Thr Arg Glu Asp Lys Asn Ser Asn
            20                  25                  30

Ala Gly Tyr Thr Asp Pro Val Thr Gly Lys Thr Thr Met Asn Pro Trp
        35                  40                  45

Thr Pro Ala Lys Gln Gly Leu Arg Ala Val Asn Val Glu Gln Ile Lys
    50                  55                  60

Gly Tyr Val Ala Lys Val Asp Gly Asn Val Asp Ala Val Val Val Thr
65                  70                  75                  80

Pro Asp Ser Ala Asn Met Val Val Thr Ile Thr Tyr Gln Ala Asn Lys
                85                  90                  95

Pro Glu Gly Gln Asn Ile Thr Val Lys Lys Asp Thr Val Pro Asp Pro
            100                 105                 110

Ala Asp Gly Ile Lys Asn Lys Asp Asp Leu Pro Asp Gly Thr Lys Tyr
        115                 120                 125

Thr Trp Lys Glu Val Pro Asp Val Asn Ser Val Gly Glu Lys Thr Gly
    130                 135                 140

Ile Val Thr Val Thr Phe Pro Asp Gly Thr Ser Val Asp Val Lys Val
145                 150                 155                 160

Thr Val Tyr Val Asp Pro Val Val Glu Ser Asn Arg Asp Thr Leu Ser
                165                 170                 175

Lys Glu Ala Asn Thr Gly Asn Thr Asn Val Ala Lys Ala Ala Thr Val
            180                 185                 190

Thr Ser Ser Lys Val Glu Ser Lys Lys Thr Leu Pro Gln Thr Gly Ser
        195                 200                 205

Lys Thr Glu Gln Val Gly Ile Leu Gly Leu Ala Ile Ala Thr Val Gly
    210                 215                 220

Ser Leu Leu Gly Leu Gly Val Asn Arg Lys Lys Arg Gln Lys
225                 230                 235

<210> SEQ ID NO 5
<211> LENGTH: 235
<212> TYPE: PRT
<213> ORGANISM: Artificial Sequence
<220> FEATURE:
<223> OTHER INFORMATION: Description of Artificial Sequence:anchor
      sequence

<400> SEQUENCE: 5

Lys Lys Ala Glu Glu Val Lys Asn Asn Ser Asn Ala Thr Gln Lys Glu
 1               5                  10                  15

Val Asp Asp Ala Thr Asn Asn Leu Lys Gln Ala Gln Asn Asp Leu Asp
            20                  25                  30

Gly Gln Thr Thr Asp Lys Ser Lys Leu Asp Glu Ala Ile Lys Ser Ala
        35                  40                  45

Asp Asp Thr Lys Ser Thr Asp Lys Tyr Asn Asn Ala Ser Asp Asp Thr
    50                  55                  60
```

Lys Ser Lys Phe Asp Glu Ala Leu Lys Ala Glu Val Lys Asn
 65                  70                  75                  80

Asn Ser Asn Ala Thr Gln Lys Glu Val Asp Asp Ala Thr Lys Asn Leu
                 85                  90                  95

Lys Gln Ala Gln Asn Asp Leu Asp Gly Gln Thr Thr Asn Lys Asp Ala
            100                 105                 110

Ile Asn Asp Ala Ile Lys Asp Ala Asn Asn Ala Lys Gly Thr Asp Lys
            115                 120                 125

Tyr Asn Asn Ala Ser Asp Asp Thr Lys Ser Lys Phe Asp Asp Ala Leu
            130                 135                 140

Lys Lys Ala Glu Asp Val Lys Asn Asp Ser Asn Ala Asn Gln Lys Glu
145                 150                 155                 160

Val Asp Asp Ala Thr Lys Asn Leu Lys Asn Thr Leu Asn Asn Leu Lys
                165                 170                 175

Gly Gln Pro Ala Lys Lys Ala Asn Leu Ile Ala Ser Lys Asp Asn Ala
            180                 185                 190

Lys Ile His Lys Gln Thr Leu Leu Pro Gln Thr Gly Thr Glu Thr Asn
            195                 200                 205

Pro Leu Thr Ala Ile Gly Ile Gly Leu Met Ala Leu Gly Ala Gly Ile
210                 215                 220

Phe Ala Lys Lys Lys Arg Lys Asp Asp Glu Ala
225                 230                 235

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer P-59.f

<400> SEQUENCE: 6
ggcgagctcc ccaaagaagc gcgtaatatc                                    30

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:PCR
      amplification oligonucleotide primer P-59.r

<400> SEQUENCE: 7
ggaaacacgc tagcactaac ttcatt                                        26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer P-23.f

<400> SEQUENCE: 8
gtggagctcc ccgaaaagcc ctgacaaccc                                    30

<210> SEQ ID NO 9
<211> LENGTH: 26
<212> TYPE: DNA
<213> ORGANISM: Artificial Sequence
<220> FEATURE:

```
<223> OTHER INFORMATION: Description of Artificial Sequence:PCR
      amplification oligonucleotide primer P-23.r

<400> SEQUENCE: 9
ggaaacacgc tagcactaac ttcatt                                          26

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer 2D-CD4.f

<400> SEQUENCE: 10
gcggctagca agaaagttgt tttaggtaaa                                      30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer 2D-CD4.r

<400> SEQUENCE: 11
gcacaattgt gatgcctttt gaaaagctaa                                      30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:PCR
      amplification oligonucleotide primer CbsAss.f

<400> SEQUENCE: 12
gcgaattcaa ggaggaaaag accacat                                         27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:PCR
      amplification oligonucleotide primer CbsAss.r

<400> SEQUENCE: 13
ccagctagct gaaacagtag aaacggc                                         27

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:PCR
      amplification oligonucleotide primer
      HveC V & gamma.f

<400> SEQUENCE: 14
ggcgctagcc aggtggtcca ggtgaacgac tcc                                  33

<210> SEQ ID NO 15
<211> LENGTH: 33
<212> TYPE: DNA
<213> ORGANISM: Artificial Sequence
<220> FEATURE:
```

-continued

```
<223> OTHER INFORMATION: Description of Artificial Sequence:PCR
      amplification oligonucleotide primer HveC V.r

<400> SEQUENCE: 15
ccgcaattgc atcaccgtga gattgagctg gct                               33

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer HveC gamma.r

<400> SEQUENCE: 16
gcgcaattgg aacatcctag ctcttgtcct                                   30

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:cell-wall
      anchor sorting signal of M6 protein (emm6) of
      Streptococcus pyogenes
<220> FEATURE:
<221> NAME/KEY: MOD_RES
<222> LOCATION: (3)
<223> OTHER INFORMATION: Xaa = any amino acid

<400> SEQUENCE: 17

Leu Pro Xaa Thr Gly
  1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:cell-wall
      anchor sortase motif for PrtP protease of
      Lactobacillus paracasei

<400> SEQUENCE: 18

Leu Pro Lys Thr Ala
  1               5
```